(12) United States Patent
Girardot et al.

(10) Patent No.: US 6,322,271 B1
(45) Date of Patent: Nov. 27, 2001

(54) APPLICATOR FOR APPLYING AND DISTRIBUTING SUBSTANCES TO TARGET SURFACES

(75) Inventors: Richard Michael Girardot; Gene Michael Altonen, both of West Chester; Joshua James Davidson, Cincinnati; Lisa Ann Runtz, Fairfield; Drew Douglas Setser, Cincinnati, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/636,526

(22) Filed: Aug. 10, 2000

Related U.S. Application Data

(63) Continuation-in-part of application No. 09/185,785, filed on Nov. 4, 1998.

(51) Int. Cl.$^7$ ..................................................... B43K 23/12

(52) U.S. Cl. .......................... 401/262; 401/265; 401/261

(58) Field of Search .................................. 401/132, 261, 401/262, 265, 266, 49, 156

(56) References Cited

U.S. PATENT DOCUMENTS

| | | |
|---|---|---|
| 926,462 | 6/1909 | Blowers . |
| 1,431,210 | 10/1922 | Blanchard . |
| 1,511,969 | 10/1924 | Hoy . |
| 1,690,960 | 11/1928 | Yamanaka . |
| 1,705,249 | 3/1929 | Henry . |
| 1,836,833 | 12/1931 | Ames . |
| 1,925,019 | 8/1933 | Wilson . |

(List continued on next page.)

FOREIGN PATENT DOCUMENTS

| | | |
|---|---|---|
| 196 33 687 A1 | 2/1998 | (DE) . |
| 0 028 853 | 5/1981 | (EP) . |
| 0 600 508 A1 | 6/1994 | (EP) . |
| 0 732 273 B1 | 9/1996 | (EP) . |
| 0 803 210 A1 | 10/1997 | (EP) . |
| 797369 | 4/1936 | (FR) . |
| 2 601 865 | 1/1988 | (FR) . |
| 1454403 | 11/1976 | (GB) . |
| WO 96/04884 | 2/1996 | (WO) . |
| WO 97/28718 | 8/1997 | (WO) . |

Primary Examiner—David J. Walczak
(74) Attorney, Agent, or Firm—Jack L. Oney, Jr.

(57) ABSTRACT

An applicator for applying and distributing a substance onto a target surface. The applicator comprises a substantially planar sheet of conformable material having opposed first and second surfaces and an interior region between said first and second surfaces. The sheet of material has a thickness between the first and second surfaces. The applicator further includes at least one discrete reservoir underneath the first surface which is at least partially filled with a substance and at least one discrete aperture formed in the first surface which is in fluid communication with the reservoir. Compression of the applicator via an externally-applied force substantially normal to said first surface expresses product from the aperture and translational motion of the first surface relative to a target surface applies and distributes said product onto the target surface. A removable cover sheet which aids in the containment of the substance and also contributes to a pre-removal stiffness value for the applicator such that the pre-removal stiffness value is at least three times greater than a post-removal stiffness value for the applicator. The stiffness of the removable cover sheet can also provide protection against bending that could lead to failure of the containment, against puncture, and against other damage to the product rheology, homogeneity, etc. A wide variety of substances are contemplated, including particularly antiperspirant/deodorant products.

26 Claims, 3 Drawing Sheets

U.S. PATENT DOCUMENTS

| | | | |
|---|---|---|---|
| 2,044,428 | * 6/1936 | Gilmer | 15/227 |
| 2,121,701 | 6/1938 | Landers . | |
| 2,157,543 | 5/1939 | Kingman . | |
| 2,165,420 | 7/1939 | Seifert . | |
| 2,187,163 | 1/1940 | Langer . | |
| 2,190,376 | 2/1940 | Daley . | |
| 2,319,873 | 5/1943 | Linz . | |
| 2,390,921 | 12/1945 | Clark . | |
| 2,419,896 | 4/1947 | Hobelmann . | |
| 2,528,812 | 11/1950 | Berman . | |
| 2,576,834 | 11/1951 | Hensgen . | |
| 2,835,911 | 5/1958 | Mahmarian . | |
| 2,878,967 | * 2/1959 | Duke | 222/107 |
| 2,932,841 | 4/1960 | Graves . | |
| 3,006,023 | 10/1961 | Worthington . | |
| 3,007,192 | 11/1961 | Quoss . | |
| 3,053,385 | 9/1962 | Spees . | |
| 3,143,276 | 8/1964 | Nichols . | |
| 3,214,783 | 11/1965 | Perry et al. . | |
| 3,369,709 | * 2/1968 | Clauss | 222/107 |
| 3,386,793 | 6/1968 | Stanton . | |
| 3,472,675 | 10/1969 | Gordon et al. . | |
| 3,491,396 | 1/1970 | Eannarino et al. . | |
| 3,630,346 | 12/1971 | Burnside . | |
| 3,647,305 | 3/1972 | Baker et al. . | |
| 3,707,012 | 12/1972 | Lane . | |
| 3,806,260 | 4/1974 | Miller . | |
| 3,826,259 | 7/1974 | Bailey . | |
| 3,899,080 | 8/1975 | Brunda . | |
| 3,969,026 | 7/1976 | Johnson . | |
| 4,007,838 | 2/1977 | Awad . | |
| 4,111,666 | 9/1978 | Kalbow . | |
| 4,127,339 | 11/1978 | Malacheski et al. . | |
| 4,142,334 | 3/1979 | Kirsch et al. . | |
| 4,304,562 | 12/1981 | Bolan . | |
| 4,420,080 | 12/1983 | Nakamura . | |
| 4,422,546 | 12/1983 | Charity . | |
| 4,515,703 | 5/1985 | Haq . | |
| 4,596,481 | 6/1986 | Tanaka . | |
| 4,627,129 | 12/1986 | Wittes . | |
| 4,643,725 | 2/1987 | Schlesser et al. . | |
| 4,665,580 | 5/1987 | Morris . | |
| 4,683,001 | 7/1987 | Floyd . | |
| 4,706,693 | 11/1987 | Spector . | |
| 4,735,335 | 4/1988 | Torterotot . | |
| 4,738,887 | 4/1988 | Govertsen . | |
| 4,739,879 | 4/1988 | Nakamura . | |
| 4,751,934 | 6/1988 | Moir et al. . | |
| 4,762,124 | 8/1988 | Kerch et al. . | |
| 4,776,356 | 10/1988 | Jou et al. . | |
| 4,787,374 | 11/1988 | DeYarman . | |
| 4,840,270 | 6/1989 | Caputo et al. . | |
| 4,913,307 | 4/1990 | Takata et al. . | |
| 4,963,045 | 10/1990 | Willcox . | |
| 4,995,408 | 2/1991 | Wallschlaeger . | |
| 5,123,431 | 6/1992 | Wilson . | |
| 5,123,764 | 6/1992 | Duncan et al. . | |
| 5,125,529 | 6/1992 | Torterotot . | |
| 5,161,688 | 11/1992 | Munchin . | |
| 5,263,609 | 11/1993 | Hoshino . | |
| 5,373,966 | 12/1994 | O'Reilly et al. . | |
| 5,380,110 | * 1/1995 | Festa | 401/132 |
| 5,401,113 | 3/1995 | Gueret . | |
| 5,434,194 | 7/1995 | Fujimoto et al. . | |
| 5,487,932 | 1/1996 | Dunshee . | |
| 5,562,112 | 10/1996 | Gunderman et al. . | |
| 5,647,941 | * 7/1997 | Gunderman et al. | 156/277 |
| 5,904,151 | * 5/1999 | Gueret | 401/266 |

* cited by examiner

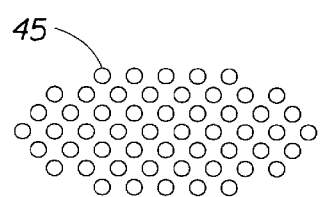
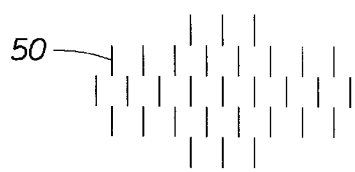
Fig. 3  Fig. 4
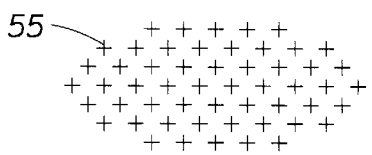
Fig. 5  Fig. 6

APPLICATOR FOR APPLYING AND DISTRIBUTING SUBSTANCES TO TARGET SURFACES

CROSS REFERENCE TO RELATED APPLICATION

This application is a continuation-in-part of prior application Ser. No. 09/185,785 filed Nov. 4, 1998.

FIELD OF THE INVENTION

The present invention relates to applicators for use in manually applying coatings of a substance onto a desired target surface. The invention also relates to products that require protective packaging against volatile losses, crushing, or other deformation. More particularly, the present invention relates to such applicators which provide both dispensing and product protection functionality and therefore enhanced product performance.

BACKGROUND OF THE INVENTION

There are many types of topical products ("products" herein interchangeably referred to as "substances") that are commercially available and/or commonly applied to a desired target surface in the form of a thin film or coating to protect, treat, modify, etc. the target surface. Such products include those in the skin care, cosmetics, pharmaceutical, and other personal care arenas. One common example of such a product is the antiperspirant/deodorant type of product, many of which are formulated as sprays, roll-on liquids, gels, creams, or solid sticks, and comprise an astringent material, e.g. zirconium or aluminum salts, incorporated into a suitable topical carrier. These products are designed to provide effective perspiration and odor control while also being cosmetically acceptable during and after application onto the axillary area or other areas of the skin. The nature of these products require protection against volatile losses and excessive deformation that can damage the product rheology, cause product separation, or otherwise harm performance.

Examples of suitable perforated caps or other shear force delivery means for use with such packaged compositions include those known in the art for application of creams, or those delivery means that are otherwise effective for delivering the composition of the present invention to the skin. Some examples of such perforated caps or other shear force delivery means, and some dispensing packages for use with compositions herein, are described in U.S. Pat. No. 5,000, 356, issued to Johnson et al. on Mar. 19, 1991, which description is incorporated herein by reference.

While such delivery means have proven successful in applying such substances and protecting against volatile losses and product separation, in many instances a comparatively complex supply mechanism is required in order to dispense the product for application by shear force delivery means. This in turn typically requires a comparatively large canister to house not only the desired quantity of product but also the product retention and supply mechanism as well. The benefit of protective functionality also typically requires even travel size canisters for both elevator-type and push-up-stick packages to have considerable weight and occupy considerable volume, thus limiting the ability of the consumer to readily transport such devices. Moreover, such constructions can limit the application feel by being hard to the touch and not conforming to the target surface Sachets, pouches, and similar small packages can be protective and contain the product, but application of products invariably gets product on hands, or is uncomfortable when the package contacts skin. These are simply small packages, and not truly applicators. Prior art discloses ways of making the packages and applicators with separate handle parts, or with separate/additional dispensing parts that are more comfortable on the skin. Addition of these parts reduce the ease of use, and sometimes require additional packaging for protection, containment, etc. Examples of these types of packages/applicators are disclosed in U.S. Pat. Nos. 4,053, 242, 4,101,053, 5,842,488, 6,026,535, and 5,904,151.

Accordingly, it would be desirable to provide such an applicator which provides a removable cover sheet which aids in the containment of the substance and also contributes to a pre-removal stiffness value for the applicator such that the pre-removal stiffness value is at least three times greater than a post-removal stiffness value for the applicator. The stiffness of the removable cover sheet can also provide protection against bending that could lead to failure of the containment, against puncture, and against other damage to the product rheology, homogeneity, etc.

SUMMARY OF THE INVENTION

The present invention provides an applicator for applying and distributing a substance onto a target surface. The applicator comprises a substantially planar sheet of conformable material having opposed first and second surfaces and an interior region between said first and second surfaces. The sheet of material has a thickness between the first and second surfaces. The applicator further includes at least one discrete reservoir underneath the first surface which is at least partially filled with a substance and at least one discrete aperture formed in the first surface which is in fluid communication with the reservoir. Compression of the applicator via an externally-applied force substantially normal to said first surface expresses product from the aperture and translational motion of the first surface relative to a target surface applies and distributes said product onto the target surface. The invention provides a removable cover sheet which aids in the containment of the substance and also contributes to a pre-removal stiffness value for the applicator such that the pre-removal stiffness value is at least three times greater than a post-removal stiffness value for the applicator. The stiffness of the removable cover sheet can also provide protection against bending that could lead to failure of the containment, against puncture, and against other damage to the product rheology, homogeneity, etc. A wide variety of substances are contemplated, including particularly antiperspirant/deodorant products.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify like elements and wherein:

FIG. 3 is a plan view similar to FIG. 1 of another embodiment of an applicator after removing the removable cover sheet;

FIG. 4 is a plan view similar to FIG. 3 of another embodiment of an applicator after removing the removable cover sheet;

FIG. 5 is a plan view similar to FIG. 3 of another embodiment of an applicator after removing the removable cover sheet;

FIG. 6 is a plan view similar to FIG. 3 of another embodiment of an applicator after removing the removable cover sheet;

DETAILED DESCRIPTION OF THE INVENTION

Figure 1:
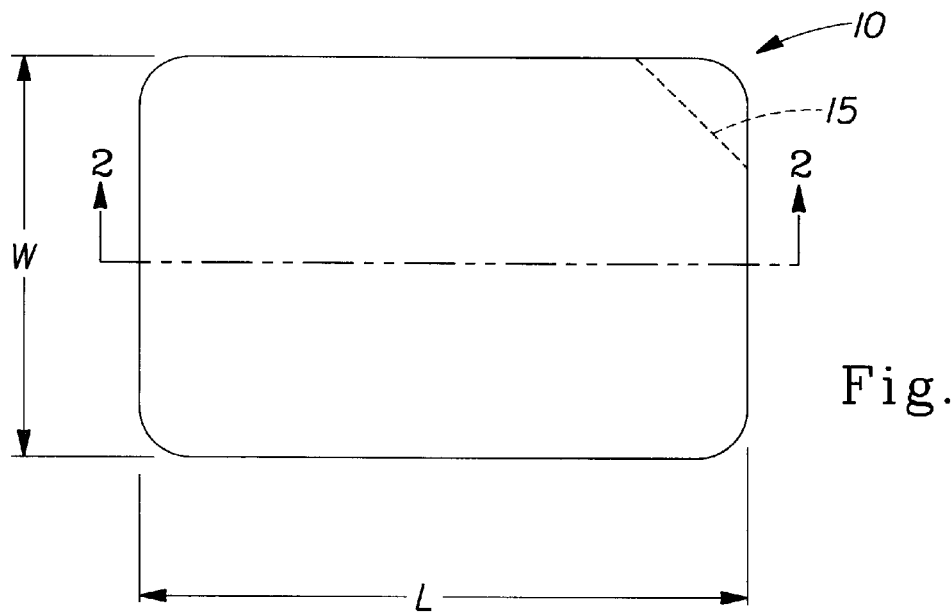
FIG. 1 is a plan view of a preferred embodiment of an applicator in accordance with the present invention.
Figure 2:
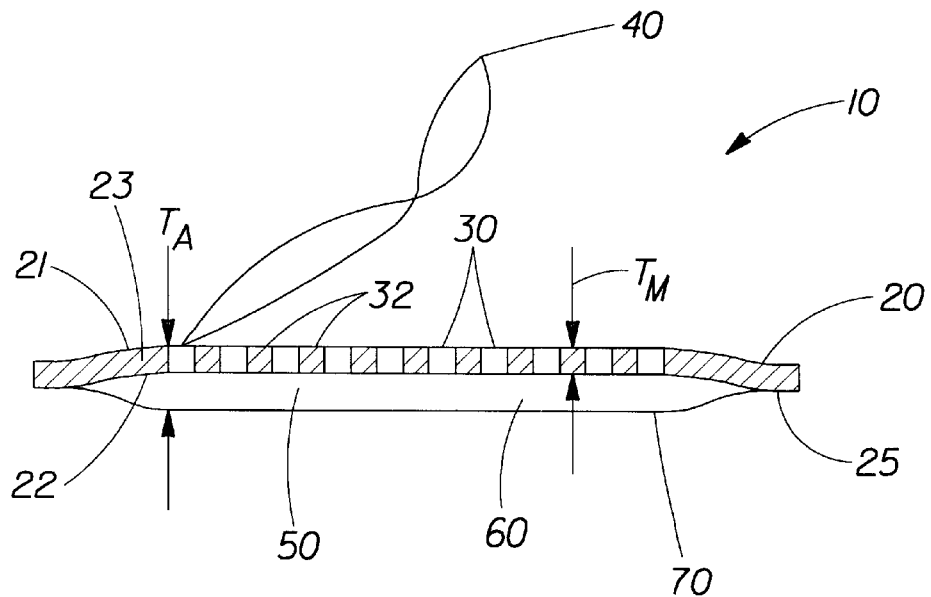
FIG. 2 is an elevational sectional view of the applicator of FIG. 1 taken along section line 2—2 with the removable cover partially removed.

FIG. 1 and FIG. 2 depict a preferred embodiment of an applicator 10 in accordance with the present invention. Applicator 10 comprises a substantially planar sheet of material 20 having a first surface 21 and a second surface 22, with the first and second surfaces defining an interior region 23 of the material 20. The first surface 21 includes at least one aperture 30, and preferably a plurality of apertures 30, which extend inwardly from the first surface 21 through the interior region 23 of the sheet of material 20 all the way through the second surface 22, such that a completely unobstructed passageway is provided through the sheet of material 20. Interstitial spaces 32 are defined between adjacent apertures 30. As will be explained hereafter, the presence and construction of the interstitial spaces 32 are believed to play an important role in the distribution performance of the applicator 10 and in turn the performance of the substance distributed. Applicator 10 also includes a removable cover sheet 40 releasably affixed to first surface 21 so as to sealingly engage the first surface over and around the apertures 30 to occlude the apertures 30 and prevent premature dispensing or contamination of the product before the intended use. Removable cover sheet 40 should be a substantially complete barrier for the product, so that the product remains contained until the product is ready to be used, the cover is removed and the applicator surface exposed. Removable cover sheet 40 can be made from a polymer film, paper, foil, metalized laminates, and combinations of these and similar materials. Removable cover sheet 40 may be adhered to the applicator surface with a heat activated peelable plastic or an adhesive which may have reuse/reseal characteristics. It is preferred to seal across the entire first surface 21 (except for a tab 15 to enable start of peeling when ready to use, or a handle [not shown]) for increased protection and stiffness, although targeted seal areas around the product area, around the apertures, and/or around the perimeter of the applicator are sometimes able to provide the desired stiffness and volatile loss barrier. Removable cover sheet 40 may comprise a label with instructions or other suitable indicia thereon. Applicator 10 also includes a backing sheet 70 which is peripherally joined to sheet of material 20 via heat sealing or any other suitable sealing technique.

Backing sheet 70 being sealed to sheet of material 20 defines a reservoir 50 for containing a substance 60 therein. The substance 60 may fill part of reservoir 50 or all of the reservoir 50. Substance 60 may fill reservoir 50 to a level at least equal to first surface 21. Substance 60 includes but is not limited to deodorant, antiperspirant, cosmetics, medicines, cleaning agents and other consumer goods.

FIG. 2 also illustrates the geometrical relationship between the apertures 30, reservoir 50, interstitial spaces 32, and the sheet material 20. The apertures, which may be of any desired size and shape, each have a peripheral edge which lies in the plane of the first surface 21 and defines the boundary of the aperture. Apertures 30 may or may not have walls which are substantially normal to the first surface of the sheet of material. The interstitial spaces 32 are thus defined as the portion of the first surface 21 located between the peripheral edges of adjacent apertures 30. Reservoir 50 is located underneath apertures 30. Reservoir 50 may or may not have the same cross-sectional shape in a direction parallel to the first surface 21 as that of the apertures 30.

The sheet of material 20 is formed from a material which is sufficiently conformable to enable the first surface 21 to conform to irregular target surfaces, and is preferably resiliently conformable for application in a dynamic environment as the first surface 21 passes over non-planar and irregular surfaces. The applicator 10, after removing the removable cover sheet 40, is also conformable in the direction of thickness $T_a$ to supply and deliver the substance 60 to the target surface for application and distribution. The reservoir 50 defines an interior volume which decreases when said applicator is compressed. Deformation of applicator 10 in such a manner effectively reduces the volume of reservoir 50 in the region of deformation, thus expressing the substance from reservoir 50 outwardly through apertures 30 into contact with the target surface.

One important characteristic for applicators of the present invention is the ability of the material to "glide" across the target surface without rolling up or otherwise becoming distorted. This also helps to ensure a comparatively even substance distribution on the target surface. Accordingly, selection of suitable applicator materials should account for not only the substance characteristics in terms of shear and other properties, but also the coefficient of friction of the material and the target surface.

The sheet of material 20 may be unitary in nature, constructed from a single monolithic piece of material, or may comprise two or more layers or plies of material. A presently preferred construction utilizes a closed cell polyethylene/EVA foam pad for the sheet of material 20. However, a wide variety of other materials are contemplated as being within the scope of the present invention having suitable physical and/or chemical properties for the intended substance and intended target surface.

Referring to FIGS. 4–6, applicator 10 may also include a plurality of semi-controlled dispensing apertures (herein interchangeably referred to as "slits") which protect the product from adherence to the removable cover sheet 40. Slits are herein defined as a cut through a substrate wherein said cut has a defined beginning and end point such that said cut has a linear dimension without fully delimiting a contained area (see slits 50, 55, 60). In contrast, a hole aperture is defined as an opening penetrating through a substrate that when viewed from a top planar perspective has a closed perimeter which delimits a contained area (see hole aperture 45).

Figure 7:
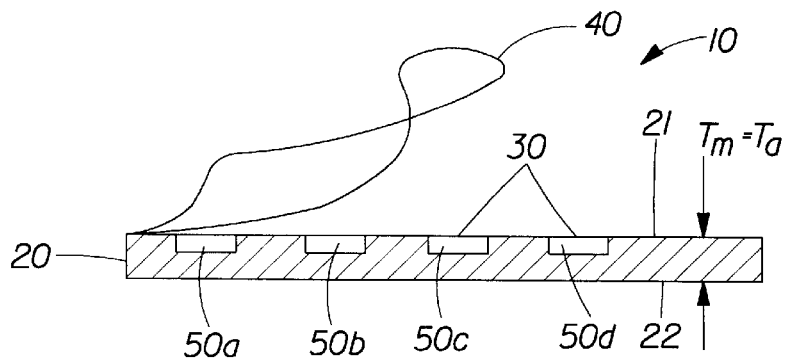
FIG. 7 is an elevational sectional view of another embodiment of an applicator.
Figure 8:
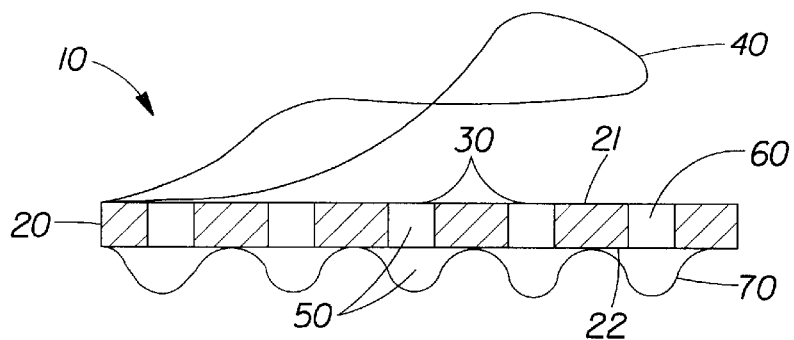
FIG. 8 is an elevational sectional view of another embodiment of an applicator.
Figure 9:
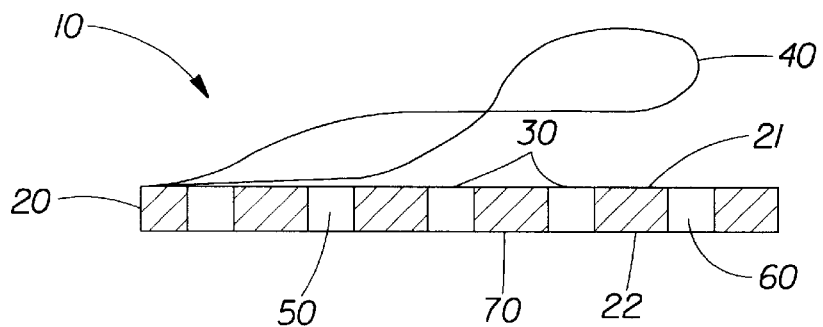
FIG. 9 is an elevational sectional view of another embodiment of an applicator.

Referring to FIGS. 7, 8, and 9, applicator 10 may include a plurality of apertures 30 and a corresponding plurality of reservoirs 50, each of said apertures being in fluid communication with one of said reservoirs 50. The plurality of reservoirs 50 may include multiple diverse substances.

Referring to FIG. 7, applicator 10 includes reservoirs 50 extending inwardly of first surface 21 into the interior of the sheet of material 20 but do not penetrate second surface 22.

The reservoirs 50 extend inwardly of first surface 21 into the interior of said sheet of material a distance which is less than the thickness $T_a$.

Figure 10:
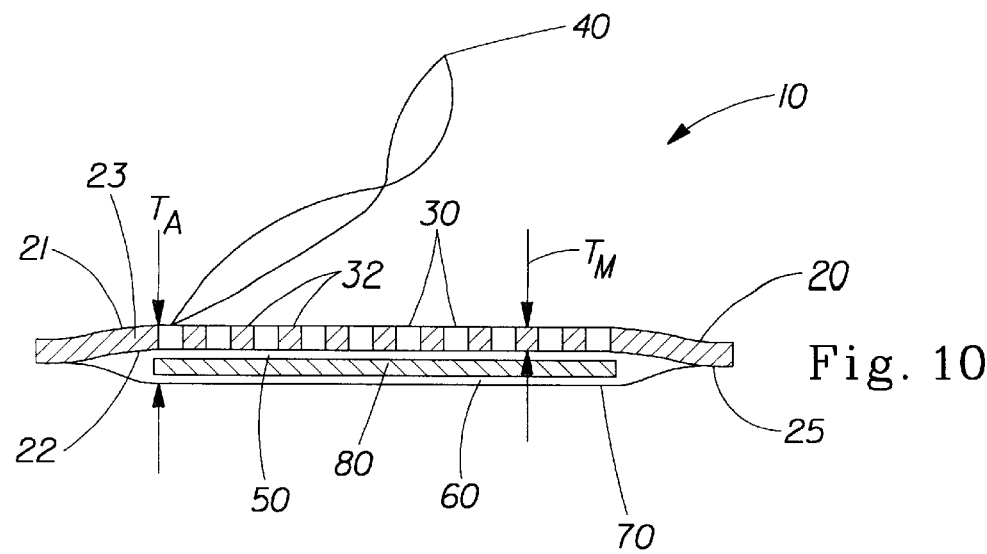
FIG. 10 is an elevational sectional view of another embodiment of an applicator having a liquid product with an absorbent structure inside the reservoir.

Referring to FIG. 10, applicator 10 includes an absorbent material 80 in the reservoir area 50 which can hold a liquid product until application force is applied.

It has been discovered that an applicator with a removable cover sheet 40, which aids in the containment of the substance and also contributes to a pre-removal stiffness value for the applicator such that the pre-removal stiffness value is at least three times greater than a post-removal stiffness value for the applicator, provides nonobvious benefits of ease use, product protection, reduced package waste, and economic advantages over other approaches. More specifically, prior to the removal of cover sheet 40, the applicator 10 may be characterized as having a pre-removal stiffness value preferably from about 45 taber to about 150 taber, and most preferably 79 taber. Once the removable cover sheet has been removed, the applicator 10 may be characterized as having a post-removal stiffness value preferably from about 1 taber to about 15 taber, and most preferably 6 taber. One skilled in the art would appreciate that the actual pre- and post-removal stiffness values may vary but that the important factor is the fact that the pre-removal stiffness value is at least three times greater than the post-removal stiffness value, more preferably ten times greater than, and most preferably twenty times greater than.

The pre-removal stiffness helps maintain the functionality of the seal during storage and helps protect against bending or puncturing that could otherwise break the seal. This pre-removal stiffness enables applicator 10 to be easily transported in a wallet, purse, glove compartment, etc. The post-removal stiffness is sufficiently flexible to allow applicator 10 to be applied and subsequently conform to the target surface.

To quantify stiffness, a suitable method is TAPPI T489 om-92, Stiffness of paper and paperboard (Taber-type stiffness tester). Results are in gram centimeters or Taber units. Equipment used; Taber V-5 model 150B Stiffness Tester.

As mentioned previously, it is presently preferred that applicator 10 without removable cover sheet 40 is not only compressible in the thickness direction but also conformable in the planar direction so as to accommodate various target surface topographies in use. It is also preferred that suitable sheet materials also be resilient, preferably both in terms of their compressibility and in terms of their bending conformability. Resilience is defined consistent with its everyday meaning, as evidenced by *Webster's Ninth New Collegiate Dictionary*, as "the capability of a strained body to recover its size and shape after deformation caused esp. by compressive stress." Resilience of the material causes it to tend to return to its undeformed, preferably substantially planar state and original thickness after compressive or bending forces, thereby enabling it to conform to various target surfaces and yet maintain target surface contact for proper substance distribution.

A preferred material for construction of the sheet of material 20 is Volara 6E0 1/32" PE/EVA polyethylene/ethylene vinyl acetate copolymer (12%VA) fine-cell crosslinked polymer foam, commercially available from Voltek, 100 Shepard Street, Lawrence, Mass. 01843. The material properties of Volara 6EO are as follows:

| Properties | Volara 6E0 1/32" | Preferred range of most foams | Test Method |
| --- | --- | --- | --- |
| Thickness (in.) | 0.03 | 0.015–0.250 | ASTM D-3575 |
| Density (lbs/cu ft) | 6 nominal | 2–20 | ASTM D-3575 |
| Tensile Str MD (psi) | 217 minimum | 40–1000 | ASTM D-3575 |
| Break Elongation MD (%) | 348 minimum | 100–600 | ASTM D-3575 |
| Compression deflection @ 25% deflection (psi) | 8 | 0–15 | ASTM D-3575 |

While Volara 6EO is the presently preferred material for the sheet of material 20, alternate Volara grades and alternate materials such as open cell foam, non-crosslinked foam, foam with a range of cell sizes, alternate resins, 100% polyethylene, polystyrene, polypropylene, rubber, urethanes, other ethylene copolymers, propylene copolymers, non-wovens, films, apertured films, woven materials, and other materials having similar material properties could be used. Note, however, for some applications materials being substantially stiffer or softer may be preferred.

A preferred material for construction of the removable cover sheet 40 is Pechiney M-9325 heat seal foil laminate consisting of 48 gauge polyester, 1.5 lbs/ream adhesive, 35 or 100 gauge foil, and 3 lbs/reampolyester based heat seal coating, commercially available from Pechiney Plastic Packaging, Inc., 2301 Industrial Drive, Neenah, Wis. 54956

While Pechiney M-9325 is presently preferred material for the removable cover sheet 40, alternate peelable seal materials available from Pechiney and other suppliers and alternate peelable seal materials such as adhesive coated films or laminates made from paper, plastic, foil, or other metallized films, and combinations of these or similar materials could be used.

A preferred material for construction of the backing sheet 70 is Curlam Grade 5378 Protective Packaging Film consisting of 48 gauge PET, 9.0 lbs/ream coex laminate, 0.000285" Foil, 12.0 lbs/ream Coex Laminate, and 1.5 or 2.0 mil LLDPE available commercially from The Curwood Group, 2200 Badger Avenue, Oshkosh, Wis. 54903

While Curlam Grade 5378 is the presently preferred material for the backing sheet 70, alternate film materials available from Curwood and other suppliers, such as heat seal or adhesive coated films or laminates made from paper, plastic, foil, or other metallized films, and combinations of these or similar materials could be used.

A preferred material for the substance 60 is a soft solid antiperspirant product formulation consisting of antiperspirant active, thickeners, solvents, and perfume. Other suitable materials for the substance 60 include antiperspirant liquid formulations, other liquids, lotions, creams, semisolids, and even solids (as a powder). When using a liquid substance it may be appreciated that a liquid-absorbing material (e.g. sponge) may be placed within reservoir 50 to contain said liquid substance until compression is asserted applicator 10 for dispensing.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. An applicator for applying and distributing a substance onto a target surface, said applicator comprising:
   a) a substantially planar sheet of conformable material having opposed first and second surfaces and an interior region between said first and second surfaces;
   b) at least one discrete reservoir underneath said first surface;
   c) a substance at least partially filling said reservoir;
   d) at least one discrete aperture formed in said first surface, said aperture being in fluid communication with said reservoir; and
   e) a removable cover sheet for enclosing said aperture prior to use, wherein said cover sheet contributes to a pre-removal stiffness value for the applicator such that the pre-removal stiffness value is at least three times greater than a post-removal stiffness value for the applicator;
   whereby compression of said applicator via an externally-applied force substantially normal to said first surface expresses said substance from said aperture and translational motion of said first surface relative to a target surface applies and distributes said substance onto said target surface.

2. The applicator of claim 1, wherein said substance fills said reservoir to a level at least equal to said first surface.

3. The applicator of claim 1, wherein said reservoir defines an interior volume which decreases when said applicator is compressed.

4. The applicator of claim 1, wherein said applicator includes a plurality of apertures.

5. The applicator of claim 1, wherein said applicator includes a plurality of reservoirs.

6. The applicator of claim 1, wherein said applicator includes a plurality of apertures and a corresponding plurality of reservoirs, each of said apertures being in fluid communication with one of said reservoirs.

7. The applicator of claim 1, wherein said aperture fully penetrates said first and second surfaces and said reservoir is formed between said second surface and a backing sheet peripherally joined thereto.

8. The applicator of claim 1, wherein said reservoir extends inwardly of said first surface into the interior of said sheet of material but does not penetrate said second surface.

9. The applicator of claim 1, wherein said reservoir extends inwardly of said first surface into the interior of said sheet of material a distance which is less than the thickness of said sheet of material.

10. The applicator of claim 1, wherein said sheet material is resilient in compression.

11. The applicator of claim 1, wherein said sheet material is resilient in bending.

12. The applicator of claim 1, wherein said sheet material comprises a closed-cell foam material.

13. The applicator of claim 1, wherein said applicator includes a plurality of reservoirs and a corresponding plurality of apertures, and wherein said reservoirs include multiple diverse substances.

14. The applicator of claim 1, wherein said applicator has a pre-removal stiffness value preferably from about 45 taber to about 150 taber, and most preferably 79 taber.

15. The applicator of claim 1, wherein said applicator has a post-removal stiffness value preferably from about 1 taber to about 15 taber, and most preferably 6 taber.

16. The applicator of claim 1, wherein said applicator has a pre-removal stiffness value which is at least ten times greater than a post-removal stiffness value for the applicator.

17. The applicator of claim 1, wherein said applicator has a pre-removal stiffness value which is at least twenty times greater than a post-removal stiffness value for the applicator.

18. An applicator for applying and distributing a substance onto a target surface, said applicator comprising:
   a) a substantially planar sheet of conformable material having opposed first and second surfaces and an interior region between said first and second surfaces;
   b) at least one discrete reservoir underneath said first surface;
   c) a substance at least partially filling said reservoir;
   d) at least one discrete aperture formed in said first surface, said aperture being in fluid communication with said reservoir; and
   e) a removable cover sheet for enclosing said aperture prior to use, wherein said cover sheet contributes to a pre-removal stiffness value for the applicator such that the pre-removal stiffness value is at least three times greater than a post-removal stiffness value for the applicator;
   whereby compression of said applicator via an externally-applied force substantially normal to said first surface expresses said substance from said aperture and translational motion of said first surface relative to a target surface applies and distributes said substance onto said target surface;
   wherein said applicator has a pre-removal stiffness value preferably from about 45 taber to about 150 taber, and most preferably 79 taber.

19. The applicator of claim 18, wherein said substance is an antiperspirant, deodorant, lotion, cream, or cosmetic.

20. The applicator of claim 18, wherein a liquid-absorbing material is positioned within said reservoir substance in order to contain a liquid substance.

21. The applicator of claim 1, wherein said applicator has a post-removal stiffness value preferably from about 1 taber to about 15 taber, and most preferably 6 taber.

22. An applicator for applying and distributing a substance onto a target surface, said applicator comprising:
   a) a substantially planar sheet of conformable material having opposed first and second surfaces and an interior region between said first and second surfaces;
   b) at least one discrete reservoir underneath said first surface;
   c) a substance at least partially filling said reservoir;
   d) at least one discrete aperture formed in said first surface, said aperture being in fluid communication with said reservoir; and
   e) a removable cover sheet for enclosing said aperture prior to use, wherein said cover sheet contributes to a pre-removal stiffness value for the applicator such that the pre-removal stiffness value is at least three times greater than a post-removal stiffness value for the applicator;
   whereby compression of said applicator via an externally-applied force substantially normal to said first surface expresses said substance from said aperture and translational motion of said first surface relative to a target surface applies and distributes said substance onto said target surface;
   wherein said applicator has a pre-removal stiffness value which is at least ten times greater than a post-removal stiffness value for the applicator.

23. The applicator of claim 22, wherein said substance is an antiperspirant, deodorant, lotion, cream, or cosmetic.

24. The applicator of claim 22, wherein a liquid-absorbing material is positioned within said reservoir substance in order to contain a liquid substance.

25. The applicator of claim 1, wherein said substance is an antiperspirant, deodorant, lotion, cream, or cosmetic.

26. The applicator of claim 1, wherein a liquid-absorbing material is positioned within said reservoir substance in order to contain a liquid substance.

* * * * *